US009221757B2

(12) United States Patent
Sanford et al.

(10) Patent No.: US 9,221,757 B2
(45) Date of Patent: Dec. 29, 2015

(54) PROCESS FOR FLUORINATING COMPOUNDS

(71) Applicant: The Regents of the University of Michigan, Ann Arbor, MI (US)

(72) Inventors: Melanie Sanford, Ann Arbor, MI (US); Shin Hee Lee, Ann Arbor, MI (US); Laura Allen, Ypsilanti, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 14/539,700

(22) Filed: Nov. 12, 2014

(65) Prior Publication Data

US 2015/0133673 A1    May 14, 2015

Related U.S. Application Data

(60) Provisional application No. 61/902,981, filed on Nov. 12, 2013.

(51) Int. Cl.
*C07D 213/803* (2006.01)
*C07D 213/79* (2006.01)

(52) U.S. Cl.
CPC .................. *C07D 213/803* (2013.01)

(58) Field of Classification Search
CPC .................................... C07D 213/803
USPC ........................................ 546/327
See application file for complete search history.

(56) References Cited

U.S. PATENT DOCUMENTS

| 7,592,486 | B2 | 9/2009 | DiMagno et al. | |
|---|---|---|---|---|
| 7,939,697 | B2 * | 5/2011 | Hagiya | 570/127 |
| 2004/0144947 | A1 * | 7/2004 | Garayt et al. | 252/1 |
| 2006/0009643 | A1 * | 1/2006 | Pleschke et al. | 544/334 |
| 2012/0190857 | A1 * | 7/2012 | Arndt et al. | 546/289 |
| 2012/0190858 | A1 * | 7/2012 | Zhu et al. | 546/289 |
| 2012/0190859 | A1 * | 7/2012 | Zhu et al. | 546/289 |
| 2012/0190860 | A1 * | 7/2012 | Whiteker et al. | 546/310 |
| 2014/0031556 | A1 * | 1/2014 | Renga et al. | 546/310 |
| 2014/0031558 | A1 * | 1/2014 | Renga et al. | 546/327 |
| 2014/0171650 | A1 * | 6/2014 | Giampietro et al. | 546/250 |
| 2014/0171653 | A1 * | 6/2014 | Renga et al. | 546/310 |
| 2014/0171654 | A1 * | 6/2014 | Johnson et al. | 546/310 |
| 2014/0206881 | A1 * | 7/2014 | Zhu et al. | 546/310 |

(Continued)

FOREIGN PATENT DOCUMENTS

EP    0146924 A2    12/1984
EP    1698606 A1    9/2006

(Continued)

OTHER PUBLICATIONS

Liang; Angewandte Chemie International Edition, 2013, 52, 8214-8264.*

(Continued)

*Primary Examiner* — Janet L Andres
*Assistant Examiner* — Daniel Carcanague
(74) *Attorney, Agent, or Firm* — Meunier Carlin & Curfman LLC

(57) ABSTRACT

Methods of preparing a fluorinated substrate by combining potassium fluoride, imidazolium salt, and a substrate substituted with at least one chloro, bromo, sulfonyl, or nitro group to thereby provide the fluorinated substrate are disclosed.

15 Claims, 1 Drawing Sheet

(56) References Cited

U.S. PATENT DOCUMENTS

| | | | | |
|---|---|---|---|---|
| 2014/0296533 A1* | 10/2014 | Renga et al. | .................. | 546/250 |
| 2015/0133672 A1* | 5/2015 | Allen et al. | .................. | 546/327 |
| 2015/0141654 A1* | 5/2015 | Allen et al. | .................. | 546/327 |

FOREIGN PATENT DOCUMENTS

| | | | |
|---|---|---|---|
| WO | 02092608 | A2 | 11/2002 |
| WO | 03076366 | A2 | 9/2003 |
| WO | 03106379 | A1 | 12/2003 |
| WO | WO 03/106379 | * | 12/2003 |
| WO | 2004048350 | A2 | 6/2004 |
| WO | 2006055748 | A2 | 5/2006 |
| WO | 2012163905 | A1 | 12/2012 |

OTHER PUBLICATIONS

Kim; J. Am. Chem. Soc. 2002, 124, 10278-10279.*
Zhong; Synthetic Communications, 2004, 34, 4301-4311.*
Anbarasan et al., Efficeient Synthesis of Aryl Fluorides, Angew. Chem., Int. Ed., 49:2219-2222, 2010.
Balz et al., On aromatic fluorine compounds, I.: A new process for their preparation. Ber. Deutsch. Chem Ges., 60:1186, 1927.
Barnette et al., N-Fluoro-N-alkylsulfonamides: Useful Reagents for the Fluorination of Carbanions, J. Am. Chem. Soc., 106:452-454, 1984.
Cox et al., "Anhydrous" Tetrabutylammonium Fluoride: A Mild but Highly Efficient Source of Nucleophilic Fluoride Ion, J. Org. Chem., 49:3216-3219, 1984.
Differding et al., Nucleophilic Substitution Versus Electron Transfer: 2.SH1 at Fluorine and Electron Transfer are Competing and Different Pathways in Electrophilic Fluorinations, Tetrahedron Lett., 32:3819-3822, 1991.
Heinz et al. A simple synthesis of tetraalkylammonium salts with functional anions. Justis Liebig Annalen der Chemie, 12:1937, 1978.
Higgins et al., PKas of the conjugate acids of N-heterocyclic carbenes in water, Chem. Commun., 47:1559-1561, 2011.
Okamoto et al., Activity and behavior of imidazolium salts as a phase transfer catalyst for a liquid-liquid phase system, Tetrahedron Letters, 47:8055-8058, 2006.
Sharma et al., Instability of Anhydrous Tetra-N-alkylammonium Fluorides, J. Org. Chem., 48:2112-2114, 1983.
Sun et al., Anhydrous Tetrabutylammonium Fluoride, J. Am. Chem. Soc., 127:2050-2051, 2005.
Sun et al., Room-Temperature Nucleophilic Aromatic Fluorination: Experimental and Theoretical Studies, Angewandte Chemie International Edition, 45:2720-2725, 2006.
Walsh et al., Mutations in an Auxin Receptor Homolog AFB5 and in SGT1b Confer Resistance to Synthetic Picolinate Auxins and not to 2,4-Dichlorophenoxyacetic Acid or Indole-3-Acetic Acid in Arabidopsis, Plant Physiology, 142:542-552, 2006.
Yamada et al., Convenient Electrophilic Fluorination of Functionalized Aryl and Heteroaryl Magnesium Reagents, Angew. Chem., Int. Ed., 49:2215-2218, 2010.
International Search Report and Written Opinion for PCT/US2014/065272, dated Jan. 30, 2015.
International Search Report and Written Opinion for PCT/US2014/065199, dated Jan. 30, 2015.
Bobbio et al., Removal of Fluorine from and Introduction of Flourine into Polyhalopyridines: An Exercise in Nucleophilic Hetarenic Substitution. Eur. J. Chem. 11(6):1903-1910, 2005.
Allen et al., Mild Fluorination of Chloropyridines with in situ Generated Anhydrous Tetrabutylammonium Fluoride. J. Org. Chem. 17(12):5827-5833, 2014.
Allen et al., Developing Efficient Nucleophilic Fluorination Methods and Application to Substituted Picolinate Esters. Org. Proc. Res. Dev. 18(8):1045-1054, 2014.
Sagar et al. Synthetic studies towards the antiviral pyrazine derivative T-205. Proceedings of the 13th Electronic Conference on Synthetic Organic Chemistry Nov. 1-30, 2009, 13:1-3.
Maggini et al., A general procedure for the fluorodenitration of aromatic substrates. J. Org. Chem. 56(22):6406-6411, 1991.
Sasson et al., Tetramethylammonium chloride as a selective and robust phase transfer catalyst in solid-liquid halex reaction: the role of water. Chem. Commun. 197-298, 1996.
International Search Report and Written Opinion for PCT/US2014/065212 dated Mar. 31, 2015.

* cited by examiner

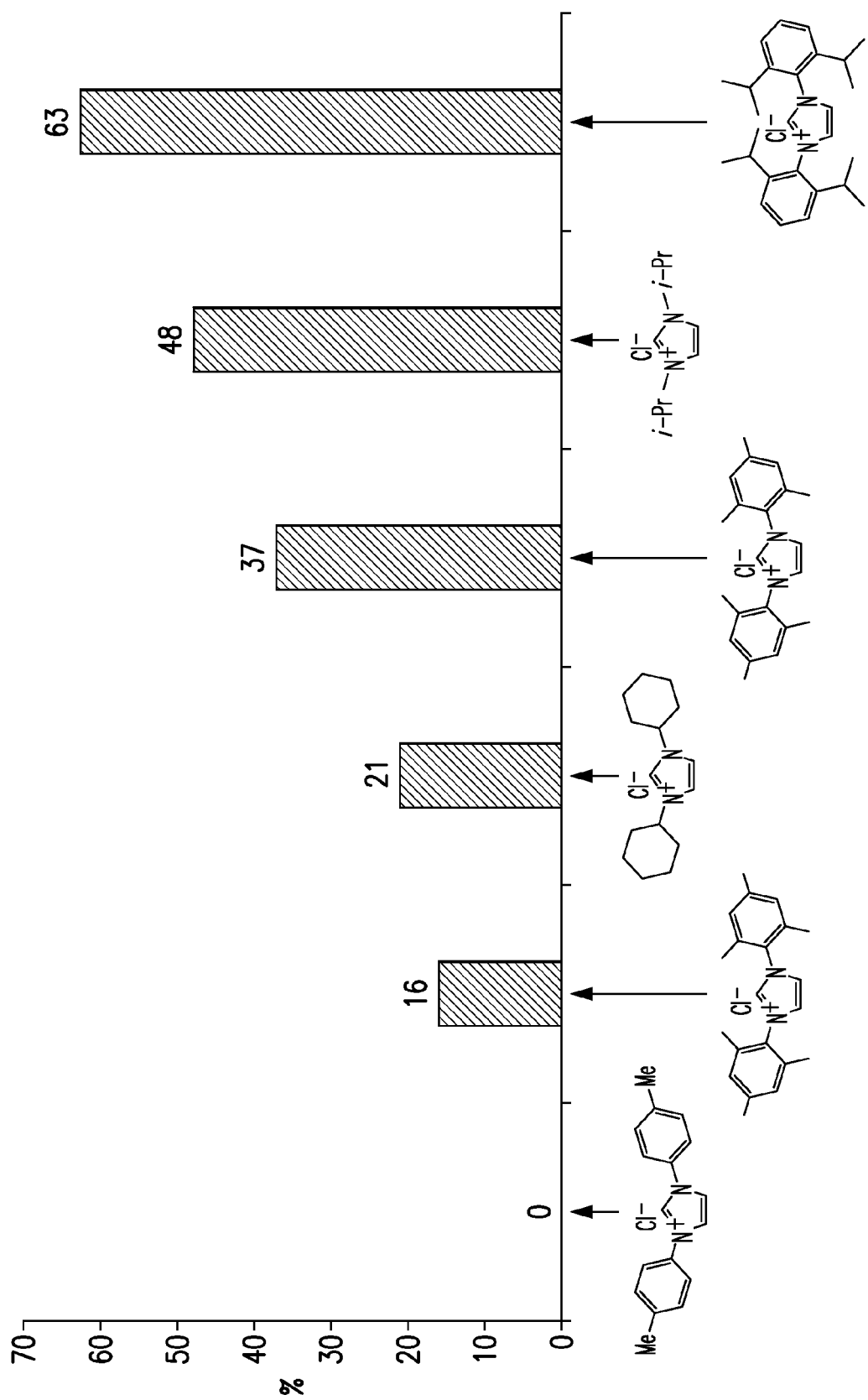

PROCESS FOR FLUORINATING COMPOUNDS

CROSS REFERENCE TO RELATED APPLICATIONS

This application claims the benefit of U.S. Provisional Patent Application Ser. No. 61/902,981 filed Nov. 12, 2013, the entire disclosure of which is expressly incorporated herein by reference.

FIELD

This application relates generally to methods of fluorinating compounds and to fluorinated compounds.

BACKGROUND

Fluorinated organic molecules are increasingly used in life science industries. The presence of a fluorine substituent can have positive effects on the biological properties of compounds. Thus, synthetic techniques for fluorinating compounds are a significant area of interest.

The selective fluorination of aryl and heteroaryl substrates is a challenging synthetic problem. As an example, mono- and di-chloro substituted picolinate esters are difficult to fluorinate and require more expensive metal fluorides (e.g., cesium fluoride (CsF)) to generate acceptable yields. Under Halex (halogen exchange) conditions, which use potassium fluoride, the chemical yields are often quite low (<20%). Also, Halex conditions usually require a phase transfer catalyst, a high boiling solvent, and high temperatures. Such conditions can preclude the use of Halex conditions in many systems. What are needed are new methods for fluorinating compounds, especially a wide variety of fluorinated compounds, and the methods and compounds disclosed herein address these and other needs.

SUMMARY

The subject matter disclosed herein relates to methods of making compositions and the compositions themselves. In particular, the subject matter disclosed herein relates generally to methods of fluorinating compounds and to fluorinated compounds. In certain specific aspects, disclosed herein are methods of preparing a fluorinated substrate that comprise combining potassium fluoride, one or more imidazolium salts, and a substrate substituted with at least one chloro, bromo, sulfonyl, or nitro group, to thereby provide the fluorinated substrate. In the disclosed methods, the potassium fluoride, imidazolium salt, and/or substrate can be combined in the presence of a solvent.

The disclosed methods are particularly well suited for fluorinating heteroaryl substrates having Formula IA or IB:

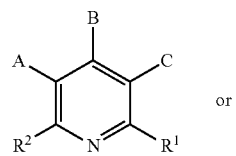

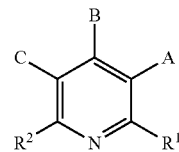

wherein A is Cl, Br, $SO_2R^8$, or $NO_2$; B is H, Cl, Br, $SO_2R^8$, or $NO_2$; C is H, Cl, Br, $SO_2R^8$, or $NO_2$; $R^1$ is H, CN, or $CO_2R^8$, wherein each $R^8$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and $R^2$ is H, substituted or unsubstituted aryl, substituted or unsubstituted heteroaryl. One of the resulting products of the disclosed methods upon substrates having Formula IA or IB is a compound having Formula IIA or IIB

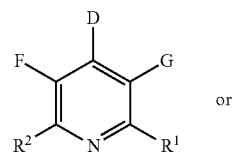

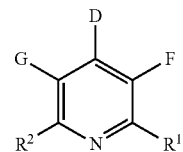

wherein D is B, as is defined above, or F; and G is B, as is defined above, or F. The disclosed products represented by Formula IIA or IIB are often obtained in greater yields than the difluorinated or para-fluorinated substrates, indicating the fluorinating process disclosed herein is relatively selective.

Various imidazolium salts can be used in the disclosed methods, such as those having an imidazolium cation having Formula A:

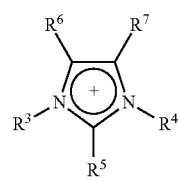

wherein $R^3$ and $R^4$ are, independently, substituted or unsubstituted $C_1$-$C_{12}$ alkyl, substituted or unsubstituted $C_1$-$C_{12}$ alkoxyalkyl, substituted or unsubstituted $C_3$-$C_8$ cycloalkyl, substituted or unsubstituted aryl, or substituted or substituted heteroaryl; and $R^5$, $R^6$, and $R^7$ are, independently, H, substituted or unsubstituted $C_1$-$C_{12}$ alkyl, substituted or unsubstituted $C_1$-$C_{12}$ alkoxy, substituted or unsubstituted $C_1$-$C_{12}$ alkoxyalkyl, substituted or unsubstituted $C_3$-$C_8$ cycloalkyl, or substituted or unsubstituted aryl. In the disclosed methods, the imidazolium cations have Formula A wherein either or both $R^3$ and $R^4$ is a substituted aryl or substituted heteroaryl group having Formula III:

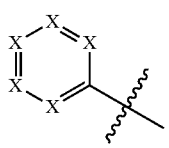

III wherein each X is, independent of the others, $CR^9$ or N; each $R^9$ is, independent of the others, H, alkyl, cycloalkyl, alkoxy, alkenyl, cycloalkenyl, alkynyl, aryl, heteroaryl, ether, hydroxy, silyl, sulfonyl, sulfone, sulfoxide, or thiol.

In other aspects, the subject matter disclosed herein relates to methods of preparing a fluorinated heteroaryl substrate that comprises mixing potassium fluoride, an imidazolium salt, a solvent, and a heteroaryl substrate having Formula IA or IB wherein A is Cl, Br, $SO_2R^8$, or $NO_2$; B is H, Cl, Br, $SO_2R^8$, or $NO_2$; C is H, Cl, Br, $SO_2R^8$, or $NO_2$; $R^1$ is H, CN, or $CO_2R^8$, wherein each $R^8$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and $R^2$ is H, substituted or unsubstituted aryl, substituted or unsubstituted heteroaryl.

In still other aspects, the subject matter disclosed herein relates to products prepared by the methods disclosed herein. In still other aspects, the subject matter disclosed herein relates to fluorinated compounds, such as those prepared by the disclosed methods.

Additional advantages of the disclosed subject matter will be set forth in part in the description that follows and the FIGURE, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURE

The accompanying FIGURE, which is incorporated in and constitutes a part of this specification, illustrates several aspects described below.

FIG. 1 is a graph showing fluorination of a model substrate, 5-chloro-6-phenylpicolinate with potassium fluoride in the presence of various imidazolium salts.

DETAILED DESCRIPTION

The materials, compounds, compositions, articles, and methods described herein may be understood more readily by reference to the following detailed description of specific aspects of the disclosed subject matter and the Examples and FIGURE included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like.

When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as $-OZ^1$ wherein $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E- and Z-isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. In certain specific examples cycloalkyl is a $C_{3-8}$ cycloalkyl.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (e.g., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula $-C(O)H$. Throughout this specification "C(O)" or "CO" is a short hand notation for C=O, which is also referred to herein as a "carbonyl."

The terms "amine" or "amino" as used herein are represented by the formula $-NZ^1Z^2$, wherein $Z^1$ and $Z^2$ can each be a substituent group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is $-C(O)NZ^1Z^2$.

The term "carboxylic acid" as used herein is represented by the formula —C(O)OH. A "carboxylate" or "carboxyl" group as used herein is represented by the formula —C(O)O⁻.

The term "ester" as used herein is represented by the formula —OC(O)Z¹ or —C(O)OZ¹, wherein Z¹ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula Z¹OZ², wherein Z¹ and Z² can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula Z¹C(O)Z², wherein Z¹ and Z² can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to fluorine, chlorine, bromine, and iodine. The corresponding term "halo", e.g., fluoro, chloro, bromo, and iodo as used herein refer to the corresponding radical or ion.

The term "hydroxyl" as used herein is represented by the formula —OH.

The term "cyano" as used herein is represented by the formula —CN. Cyanide is used to refer to the cyanide ion CN⁻.

The term "nitro" as used herein is represented by the formula —NO₂.

The term "silyl" as used herein is represented by the formula —SiZ¹Z²Z³, wherein Z¹, Z², and Z³ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)₂Z¹, wherein Z¹ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)₂NH—.

The term "thiol" as used herein is represented by the formula —SH.

The term "thio" as used herein is represented by the formula —S—.

"R¹," "R²," "R³," "Rⁿ," etc., wherein n is some integer, as used herein can, independently, possess one or more of the groups listed above. For example, if R¹ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and FIGURE.

Methods

Disclosed herein are methods of fluorinating substrates that use particular imidazolium salts in conjunction with potassium fluoride (KF) to generate the desired aromatic fluorination product in yields often similar to or better than the CsF control. The disclosed methods comprise combining potassium fluoride, one or more imidazolium salts, and a substrate substituted with at least one chloro, bromo, sulfonyl, or nitro group, to thereby provide the fluorinated substrate.

In the disclosed methods, the potassium fluoride and substrate can be combined, followed by the addition of the imidazolium salt. Alternatively, the imidazolium salt and substrate can be combined, followed by the addition of potassium fluoride. In another alternative, the potassium fluoride, substrate, and imidazolium salt can be combined simultaneously. The combination of these materials can be accomplished by methods known in the art. For example, the potassium fluoride can be added to the substrate or vice versa. Typically, the addition can be accompanied by mixing, stirring, shaking or other form of agitation. Alternatively, the imidazolium salt can be added to the substrate or vice versa. Again this addition can be accompanied by mixing, stirring, shaking or other form of agitation. In still another example, the imidazolium salt can be added to the potassium fluoride or vice versa, which can be accompanied by mixing, stirring, shaking or other form of agitation.

Further, the combination of these materials can be conducted at elevated temperature, e.g., from about 30° C. to about 225° C., from about 50° C. to about 200° C., from about 100° C. to about 150° C., from about 100° C. to about 225° C., from about 150° C. to about 225° C., from about 30° C. to about 100° C., from about 50° C. to about 100° C., from about 30° C. to about 50° C., or from about 75° C. to about 200° C. In certain examples, the materials can be combined at room temperature.

Still further, once combined, the resulting combination of potassium fluoride, substrate, imidazolium salt, and optional solvent, can be heated. The amount of heat can be adjusted depending upon the substrate and progress of the reaction, which can be monitored by methods known in the art. In general, the combination can be heated to from about 50° C. to about 250° C., from about 75° C. to about 225° C., from about 100° C. to about 200° C., from about 125° C. to about 175° C., from about 50° C. to about 150° C., from about 75° C. to about 125° C., from about 150° C. to about 250° C., or from about 100° C. to about 150° C.

The amount of potassium fluoride can vary depending on the particular substrate. In certain examples, from about 0.5 to about 10 equivalents of potassium fluoride can be used per equivalent of the substrate. For example, from about 0.5 to about 9 equivalents, from about 0.5 to about 8 equivalents, from about 0.5 to about 7 equivalents, from about 0.5 to about 6 equivalents, from about 0.5 to about 5 equivalents, from about 0.5 to about 4 equivalents, from about 0.5 to about 3 equivalents, from about 0.5 to about 2 equivalents, from about 1 to about 10 equivalents, from about 1 to about 9 equivalents, from about 1 to about 8 equivalents, from about 1 to about 7 equivalents, from about 1 to about 6 equivalents, from about 1 to about 5 equivalents, from about 1 to about 4 equivalents, from about 1 to about 3 equivalents, from about 2 to about 10 equivalents, from about 2 to about 9 equivalents, from about 2 to about 8 equivalents, from about 2 to about 7 equivalents, from about 2 to about 6 equivalents, from about 2 to about 5 equivalents, from about 2 to about 4 equivalents, from about 2 to about 3 equivalents, from about 3 to about 10 equivalents, from about 3 to about 9 equivalents, from about 3 to about 8 equivalents, from about 3 to about 7 equivalents, from about 3 to about 6 equivalents, from about 3 to about 5 equivalents, from about 3 to about 4 equivalents, from about 4 to about 10 equivalents, from about 4 to about 9 equivalents, from about 4 to about 8 equivalents, from about 4 to about 7 equivalents, from about 4 to about 6 equivalents, from about 4 to about 5 equivalents, from about 5 to about 10 equivalents, from about 5 to about 9 equivalents, from about 5 to about 8 equivalents, from about 5 to about 7 equivalents, from about 5 to about 6 equivalents, from about 6 to about 10 equivalents, from about 6 to about 9 equivalents, from about 6 to about 8 equivalents, from about 6 to about 7 equivalents, from about 7 to about 10 equivalents, from about 7 to about 9 equivalents, from about 7 to about 8 equivalents, from about 8 to about 10 equivalents, from about 8 to about 9 equivalents, from about 9 to about 10 equivalents, or from about 0.5 to about 1 equivalent of potassium fluoride can be used per equivalent of the substrate.

Imidazolium Salts

In the disclosed methods, various imidazolium salts can be used. In certain examples, the imidazolium salt can comprise an imidazolium cation having Formula A:

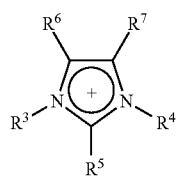

wherein $R^3$ and $R^4$ are, independently, substituted or unsubstituted $C_1$-$C_{12}$ alkyl, substituted or unsubstituted $C_1$-$C_{12}$ alkoxyalkyl, substituted or unsubstituted $C_3$-$C_8$ cycloalkyl, substituted or unsubstituted aryl, or unsubstituted or substituted heteroaryl, and $R^5$, $R^6$, and $R^7$ are, independently, H, substituted or unsubstituted $C_1$-$C_{12}$ alkyl, substituted or unsubstituted $C_1$-$C_{12}$ alkoxy, substituted or unsubstituted $C_1$-$C_{12}$ alkoxyalkyl, substituted or unsubstituted $C_3$-$C_8$ cycloalkyl, or substituted or unsubstituted aryl.

In specific examples, the imidazolium cation of Formula A can have $R^3$ and $R^4$ as, independently, substituted or unsubstituted $C_1$-$C_6$ alkyl, substituted or unsubstituted $C_3$-$C_8$ cycloalkyl, or substituted or unsubstituted aryl. In other examples, the imidazolium cation of Formula A can have $R^3$, $R^4$, or both as unsubstituted $C_3$-$C_8$ cycloalkyl, unsubstituted aryl, $C_3$-$C_8$ cycloalkyl substituted with one or more $C_1$-$C_6$ alkyl, or aryl substituted with one or more $C_1$-$C_6$ alkyl. In still further examples, the imidazolium cation of Formula A can have $R^5$, $R^6$, and $R^7$ as H.

In further specific examples, both $R^3$ and $R^4$ are $C_1$-$C_6$ alkyl, with one being methyl, and $R^5$, $R^6$, and $R^7$ are H. Exemplary $C_1$-$C_6$ alkyl groups include methyl, ethyl, propyl, isopropyl, butyl, sec-butyl, isobutyl, pentyl, isopentyl, hexyl, 2-ethylbutyl, 2-methylpentyl, cyclopentyl, cyclohexyl, and the like.

Additional examples of suitable imidazolium cations have either or both $R^3$ and $R^4$ as an aryl or heteroaryl group. For example, either or both $R^3$ and $R^4$ can have the Formula III:

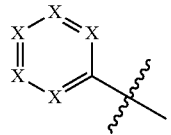

wherein each X is, independent of the others, $CR^9$ or N; each $R^9$ is, independent of the others, H, alkyl, cycloalkyl, alkoxy, alkenyl, cycloalkenyl, alkynyl, aryl, heteroaryl, ether, hydroxy, silyl, sulfonyl, sulfone, sulfoxide, or thiol. In particular examples of the imidazolium cation of Formula A, either or both $R^3$ and $R^4$ are Formula III, wherein X is $CR^9$, and each $R^9$ is, independent of the others, H or $C_1$-$C_6$ alkyl. In still further examples, Formula III is tosyl, 2,4,6-trimethylphenyl, or 2,6-di-isopropylphenyl.

In yet further examples, suitable imidazolium cations can have Formula A, wherein $R^5$, $R^6$, and $R^7$ are H, $R^3$ is chosen from methyl, ethyl, propyl, isopropyl, butyl, sec-butyl, isobutyl, pentyl, isopentyl, hexyl, 2-ethylbutyl, 2-methylpentyl, cyclopentyl, and cyclohexyl and $R^4$ is represented by Formula III. In yet further examples, suitable imidazolium cations can have Formula A, wherein $R^5$, $R^6$, and $R^7$ are H, and $R^3$ and $R^4$ each can have Formula III. In still further examples, suitable imidazolium cations can have Formula A, wherein $R^5$, $R^6$, and $R^7$ are H, and $R^3$ and $R^4$ each can have Formula III, wherein X is $CR^9$, and each $R^9$ is, independent of the others, H, methyl, ethyl, propyl, isopropyl, butyl, sec-butyl, isobutyl, pentyl, isopentyl, hexyl, 2-ethylbutyl, 2-methylpentyl, cyclopentyl, and cyclohexyl.

The imidazolium salt can have various anions in combination with the imidazolium cation. For example, the imidazolium salt can have an anion chosen from $Cl^-$, $Br^-$, and $C_1$-$C_6CO_2^-$. Other suitable anions in the imidazolium salt include, but are not limited to, $OH^-$, $I^-$, $CN^-$, $SCN^-$, $OCN^-$, $CNO^-$, $N_3^-$, $CO_3^{2-}$, $HCO_3^-$, $HS^-$, $NO_2^-$, $NO_3^-$, $SO_4^{2-}$, $PO_4^{3-}$, $PF_6^-$, $ClO^-$, $ClO_2^-$, $ClO_3^-$, $ClO_4^-$, $CF_3CO_2^-$, $CF_3SO_3^-$, $BF_4^-$, and $C_6H_6CO_2^-$. In specific examples, the imidazolium salt comprises one or more $C_1$-$C_6CO_2^-$ chosen from formate, acetate, propionate, butyrate, hexanoate, maleate, fumarate, oxalate, lactate, and pyruvate. Sulfate anions, such as tosylate, mesylate, trifluoromethanesulfonate, trifluoroethanesulfonate, di-trifluoromethanesulfonyl amino can also be used as suitable anions in the imidazolium salt.

The amount of the imidazolium salt can vary depending on the particular substrate. In certain examples, from about 0.5 to about 10 equivalents of the imidazolium salt can be used per equivalent of the substrate. For example, from about 0.5 to about 9 equivalents, from about 0.5 to about 8 equivalents, from about 0.5 to about 7 equivalents, from about 0.5 to about 6 equivalents, from about 0.5 to about 5 equivalents, from about 0.5 to about 4 equivalents, from about 0.5 to about 3 equivalents, from about 0.5 to about 2 equivalents, from about 1 to about 10 equivalents, from about 1 to about 9 equivalents, from about 1 to about 8 equivalents, from about 1 to about 7 equivalents, from about 1 to about 6 equivalents, from about 1 to about 5 equivalents, from about 1 to about 4 equivalents, from about 1 to about 3 equivalents, from about 2 to about 10 equivalents, from about 2 to about 9 equivalents, from about 2 to about 8 equivalents, from about 2 to about 7 equivalents, from about 2 to about 6 equivalents, from about 2 to about 5 equivalents, from about 2 to about 4 equivalents, from about 2 to about 3 equivalents, from about 3 to about 10 equivalents, from about 3 to about 9 equivalents, from about 3 to about 8 equivalents, from about 3 to about 7 equivalents, from about 3 to about 6 equivalents, from about 3 to about 5 equivalents, from about 3 to about 4 equivalents, from about 4 to about 10 equivalents, from about 4 to about 9 equivalents, from about 4 to about 8 equivalents, from about 4 to about 7 equivalents, from about 4 to about 6 equivalents, from about 4 to about 5 equivalents, from about 5 to about 10 equivalents, from about 5 to about 9 equivalents, from about 5 to about 8 equivalents, from about 5 to about 7 equivalents, from about 5 to about 6 equivalents, from about 6 to about 10 equivalents, from about 6 to about 9 equivalents, from about 6 to about 8 equivalents, from about 6 to about 7 equivalents, from about 7 to about 10 equivalents, from about 7 to about 9 equivalents, from about 7 to about 8 equivalents, from about 8 to about 10 equivalents, from about 8 to about 9 equivalents, from about 9 to about 10 equivalents, or from about 0.5 to about 1 equivalent of the imidazolium salt can be used per equivalent of the substrate.

Substrate

An advantage of the disclosed methods is that it can be effective at fluorinating a wide variety of substrates. It is particularly well suited for fluorinating aryl and heteroaryl substrates. In particular examples of the disclosed methods, the substrate can have Formula IA or IB:

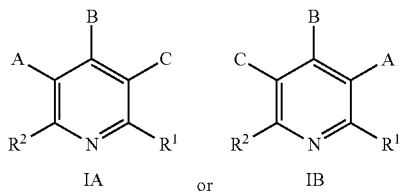

wherein
A is Cl, Br, $SO_2R^8$, or $NO_2$;
B is H, Cl, Br, $SO_2R^8$, or $NO_2$;
C is H, Cl, Br, $SO_2R^8$, or $NO_2$;
$R^1$ is H, CN, or $CO_2R^8$, wherein each $R^8$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and
$R^2$ is H, substituted or unsubstituted aryl, or substituted or unsubstituted heteroaryl.

The resulting fluorinated products can have Formula IIA or IIB

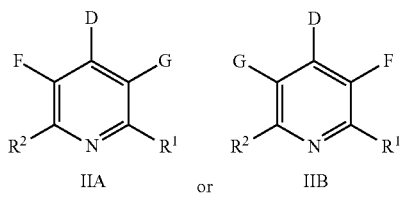

wherein D is B, as is defined above, or F; and G is B, as is defined above, or F.

The disclosed methods can be selective in that the competing product, difluorinated or a para-fluorinated products, is present in an amount less than the amount of the product of Formula IIA or IIB. For example, the amount of bisfluorinated or a para-fluorinated product is less than the amount of the product of Formula IIA or IIB when D is B and G is B, as defined above.

Solvents

Solvents can also be used in the disclosed methods. Solvents can be added to the substrate, the potassium fluoride, the imidazolium salt, or any combination of these. Suitable solvents can be polar aprotic solvents. In certain examples, the solvent can be one or more of dimethylformamide, dimethylacetamide, tetrahydrofuran, sulfolane, and deuterated analogs thereof. In particular examples, the solvent can be acetonitrile or a deuterated analog thereof. In other examples, the solvent can be dimethylsulfoxide or a deuterated analog thereof. The methods disclosed herein can use any of these solvents alone or in combination with others solvents.

If used in the disclosed methods, the amount of solvent can vary depending on the particular substrate. In certain examples, from about 0.5 to about 5 equivalents of the solvent can be used per equivalent of the substrate. For example, from about 0.5 to about 4.5 equivalents, from about 0.5 to about 4 equivalents, from about 0.5 to about 3.5 equivalents, from about 0.5 to about 3 equivalents, from about 0.5 to about 2.5 equivalents, from about 0.5 to about 2 equivalents, from about 0.5 to about 1.5 equivalents, from about 0.5 to about 1 equivalent, from about 1 to about 5 equivalents, from about 1 to about 4.5 equivalents, from about 1 to about 4 equivalents, from about 1 to about 3.5 equivalents, from about 1 to about 3 equivalents, from about 1 to about 2.5 equivalents, from about 1 to about 2 equivalents, from about 1 to about 1.5 equivalents, from about 1.5 to about 5 equivalents, from about 1.5 to about 4.5 equivalents, from about 1.5 to about 4 equivalents, from about 1.5 to about 3.5 equivalents, from about 1.5 to about 3 equivalents, from about 1.5 to about 2.5 equivalents, from about 1.5 to about 2 equivalents, from about 2 to about 5 equivalents, from about 2 to about 4.5 equivalents, from about 2 to about 4 equivalents, from about 2 to about 3.5 equivalents, from about 2 to about 3 equivalents, from about 2 to about 2.5 equivalents, from about 2.5 to about 5 equivalents, from about 2.5 to about 4.5 equivalents, from about 2.5 to about 4 equivalents, from about 2.5 to about 3.5 equivalents, from about 2.5 to about 3 equivalents, from about 3 to about 5 equivalents, from about 3 to about 4.5 equivalents, from about 3 to about 4 equivalents, from about 3 to about 3.5 equivalents, from about 3.5 to about 5 equivalents, from about 3.5 to about 4.5 equivalents, from about 3.5 to about 4.0 equivalents, from about 4 to about 5 equivalents, from about 4 to about 4.5 equivalents, or from about 4.5 to about 5 equivalents of the solvent can be used per equivalent of the substrate.

In specific examples of the disclosed methods, a fluorinated heteroaryl substrate can be prepared by steps comprising mixing potassium fluoride, one or more imidazolium salts, a solvent, and a substrate having Formula IA or IB:

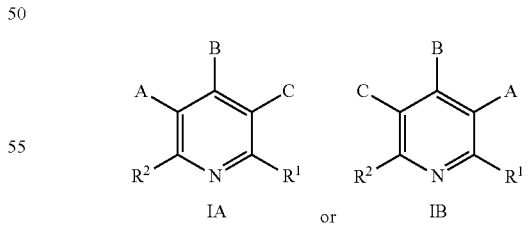

wherein
A is Cl, Br, $SO_2R^8$, or $NO_2$;
B is H, Cl, Br, $SO_2R^8$, or $NO_2$;
C is H, Cl, Br, $SO_2R^8$, or $NO_2$;
$R^1$ is H, CN, or $CO_2R^8$, wherein each $R^8$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and R² is H, substituted or unsubstituted aryl, or substituted or unsubstituted heteroaryl.

The method can use an imidazolium salt comprising an imidazolium cation having Formula A:

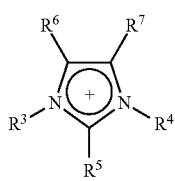

A wherein

R³ and R⁴ are, independently, substituted or unsubstituted $C_1$-$C_{12}$ alkyl, substituted or unsubstituted $C_1$-$C_{12}$ alkoxyalkyl, substituted or unsubstituted $C_3$-$C_8$ cycloalkyl, substituted or unsubstituted aryl, or substituted or unsubstituted heteroaryl; and R⁵, R⁶, and R⁷ are, independently, H, substituted or unsubstituted $C_1$-$C_{12}$ alkyl, substituted or unsubstituted $C_1$-$C_{12}$ alkoxy, substituted or unsubstituted $C_1$-$C_{12}$ alkoxyalkyl, substituted or unsubstituted $C_3$-$C_8$ cycloalkyl, or substituted or unsubstituted aryl; and an anion chosen from $Cl^-$, $Br^-$, $C_1$-$C_6CO_2^-$, $OH^-$, $I^-$, $CN^-$, $SCN^-$, $OCN^-$, $CNO^-$, $N_3^-$, $CO_3^{2-}$, $HCO_3^-$, $HS^-$, $NO_2^-$, $NO_3^-$, $SO_4^{2-}$, $PO_4^{3-}$, $ClO^-$, $ClO_2^-$, $ClO_3^-$, $ClO_4^-$, $CF_3CO_2^-$, $CF_3SO_3^-$, and $C_6H_6CO_2^-$.

The resulting fluorinated product can have Formula IIA or IIB

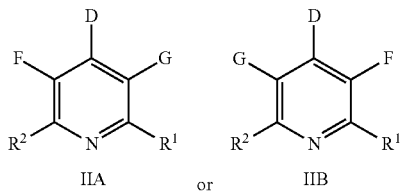

wherein D is B, as is defined above, or F; and G is B, as is defined above, or F.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in degrees Celsius (° C.) or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

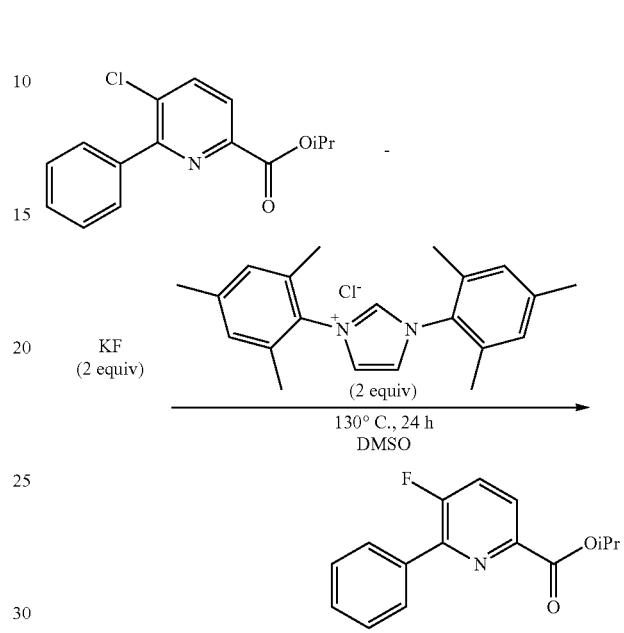

All solids (metal fluorides/phase-transfer-catalysts/additives) were weighed into a 4 mL vial equipped with a micro stirbar. To 5-chloro-6-phenylpicolinate (27.8 milligrams (mg), 0.1 millimoles (mmol), 1.00 equivalent (equiv)) was added spray-dried potassium fluoride (KF; 11.62 mg, 0.2 mmol, 2 equiv) followed by 1,3-bis(2,4,6-trimethylphenyl)-4,5-dihydroimidazolium chloride (68.2 mg, 0.2 mmol, 2.00 equiv) in the glove box (nitrogen ($N_2$) atmosphere). The solid mixture was then added with anhydrous dimethylsulfoxide (DMSO, Acros Organics AcroSeal; 0.3 mL). The vial was sealed with a Teflon-lined screwcap. The reaction vial was removed from the $N_2$ drybox and placed on an IKA™ heating/stirring plate with temperature probe, equipped with an aluminum heating block. The reaction mixture was heated/stirred at 130° C. for 24 hours (h). After stirring for 24 h, the reaction vials were cooled to room temperature, and each reaction mixture was diluted with dichloromethane ($CH_2Cl_2$; 2-3 mL). α,α,α-Trifluorotoluene (Sigma-Aldrich; 10 μL) was added as the internal standard, and yields were calculated by $^{19}F$ NMR spectroscopy.

Example 2

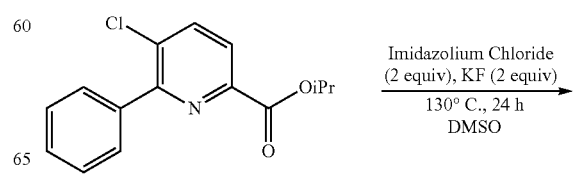

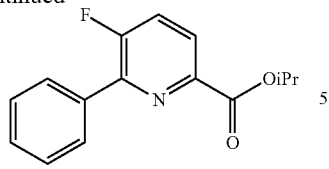

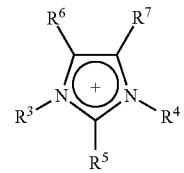

The same procedure as in Example 1 was followed, except that the imidazolium salts were varied. The salts used, and the yields, are shown in FIG. 1.

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A method of preparing a fluorinated heteroaryl substrate, comprising: mixing potassium fluoride, one or more imidazolium salts, a solvent, and a substrate having Formula IA or IB:

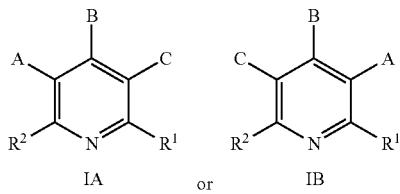

wherein

A is Cl, Br, $SO_2R^8$, or $NO_2$;

B is H, Cl, Br, $SO_2R^8$, or $NO_2$;

C is H, Cl, Br, $SO_2R^8$, or $NO_2$;

$R^1$ is H, CN, or $CO_2R^8$, wherein each $R^8$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and $R^2$ is H, substituted or unsubstituted aryl, or substituted or unsubstituted heteroaryl.

2. The method of claim 1, wherein the imidazolium salt comprises an imidazolium cation having Formula A:

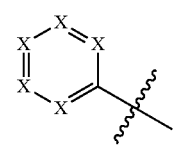

wherein $R^3$ and $R^4$ are, independently, substituted or unsubstituted $C_1$-$C_{12}$ alkyl, substituted or unsubstituted $C_1$-$C_{12}$ alkoxyalkyl, substituted or unsubstituted $C_3$-$C_8$ cycloalkyl, or substituted or unsubstituted aryl, and $R^5$, $R^6$, and $R^7$ are, independently, H, substituted or unsubstituted $C_1$-$C_{12}$ alkyl, substituted or unsubstituted $C_1$-$C_{12}$ alkoxy, substituted or unsubstituted $C_1$-$C_{12}$alkoxyalkyl, substituted or unsubstituted $C_3$-$C_8$ cycloalkyl, or substituted or unsubstituted aryl; and an anion chosen from $Cl^-$, $Br^-$, $C_1$-$C_6CO_2^-$, $OH^-$, $I^-$, $CN^-$, $SCN^-$, $OCN^-$, $CNO^-$, $N_3^-$, $CO_3^{2-}$, $HCO_3^-$, $HS^-$, $NO_2^-$, $NO_3^-$, $SO_4^{2-}$, $PO_4^{3-}$, $ClO^-$, $ClO_2^-$, $ClO_3^-$, $ClO_4^-$, $CF_3CO_2^-$, $CF_3SO_3^-$, and $C_6H_5CO_2^-$.

3. The method of claim 2, wherein, $R^3$, $R^4$, or both have Formula III:

III wherein each X is, independent of the others, $CR^9$ or N; each $R^9$ is, independent of the others, H, alkyl, cycloalkyl, alkoxy, alkenyl, cycloalkenyl, alkynyl, aryl, heteroaryl, ether, hydroxy, silyl, sulfonyl, sulfone, sulfoxide, or thiol.

4. The method of claim 2, wherein $R^3$ and $R^4$ are, independently, substituted or unsubstituted $C_1$-$C_6$ alkyl, substituted or unsubstituted $C_3$-$C_8$ cycloalkyl, or substituted or unsubstituted aryl.

5. The method of claim 2, wherein $R^3$, $R^4$, or both is unsubstituted $C_3$-$C_8$ cycloalkyl, unsubstituted aryl, $C_3$-$C_8$ cycloalkyl substituted with one or more $C_1$-$C_6$ alkyl, or aryl substituted with one or more $C_1$-$C_6$ alkyl.

6. The method of claim 2, wherein $R^5$, $R^6$, and $R^7$ are all H.

7. The method of claim 2, wherein the imidazolium salt comprises an anion chosen from $Cl^-$.

8. The method of claim 1, wherein the potassium fluoride and substrate are combined, followed by the addition of the imidazolium salt.

9. The method of claim 1, wherein the imidazolium salt and substrate are combined, followed by the addition of potassium fluoride.

10. The method of claim 1, wherein the solvent is one or more of dimethylformamide, dimethylacetamide, tetrahydrofuran, sulfolane, or deuterated analogs thereof.

11. The method of claim 1, wherein the solvent is acetonitrile or a deuterated analog thereof.

12. The method of claim 1, wherein the solvent is dimethylsulfoxide or a deuterated analog thereof.

13. The method of claim 1, further comprising heating the mixture of potassium fluoride, the imidazolium salts, and the substrate to from about 100° C. to about 150° C.

14. The method of claim 1, wherein from about 1 to about 3 equivalents of imidazolium salt is used per equivalent of the substrate.
15. The method of claim 1, wherein the fluorinated product has Formula IIA or IIB
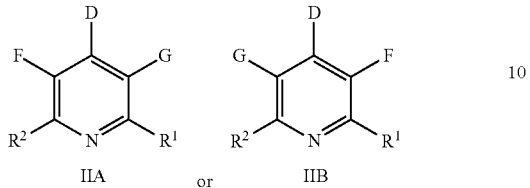
wherein D is B or F, and G is B or F, and wherein a difluorinated or a para-fluorinated product is present in an amount less than the amount of Formula IIA or IIB.
* * * * *